(12) United States Patent
Sorenson et al.

(10) Patent No.: US 8,315,445 B2
(45) Date of Patent: Nov. 20, 2012

(54) TISSUE SAMPLE IDENTIFICATION SYSTEM AND APPARATUS

(75) Inventors: Paul Sorenson, Victoria (AU); Chris Zawadzki, Victoria (AU)

(73) Assignee: Leica Biosystems Melbourne Pty Ltd, Mount Waverley (AU)

( * ) Notice: Subject to any disclaimer, the term of this patent is extended or adjusted under 35 U.S.C. 154(b) by 867 days.

(21) Appl. No.: 11/914,369

(22) PCT Filed: May 15, 2006

(86) PCT No.: PCT/AU2006/000641
§ 371 (c)(1),
(2), (4) Date: Oct. 17, 2008

(87) PCT Pub. No.: WO2006/119585
PCT Pub. Date: Nov. 16, 2006

(65) Prior Publication Data
US 2009/0214088 A1 Aug. 27, 2009

Related U.S. Application Data

(60) Provisional application No. 60/680,516, filed on May 13, 2005.

(30) Foreign Application Priority Data

May 13, 2005 (AU) ................ 2005902453

(51) Int. Cl.
*G06K 9/00* (2006.01)
*G06K 9/64* (2006.01)

(52) U.S. Cl. .......... 382/128; 382/131; 382/306; 702/19; 356/39; 600/459

(58) Field of Classification Search .......... 382/128–133, 382/306; 600/407–464; 702/19
See application file for complete search history.

(56) References Cited

U.S. PATENT DOCUMENTS 3,851,972 A * 12/1974 Smith et al. ............ 356/72
5,561,556 A * 10/1996 Weissman ............ 359/396
5,963,368 A * 10/1999 Domanik et al. ............ 359/396
6,352,861 B1 3/2002 Copeland et al.
(Continued)

FOREIGN PATENT DOCUMENTS
WO WO 03/045560 A2 6/2003

OTHER PUBLICATIONS
Supplementary European Search Report completed May 4, 2011 in European Application No. 06721511.1.

*Primary Examiner* — Jermele M Hollington
*Assistant Examiner* — Emily Chan
(74) *Attorney, Agent, or Firm* — Sughrue Mion, PLLC (57) ABSTRACT

A method an apparatus for identifying slides is disclosed, where samples such as tissue sample mounted to slides are labeled with information, and an image of the information is captured by a processing instrument. The image is analyzed, for example using optical character recognition, and information extracted from the image is used to determine the test to be applied to the slide by the processing instrument. Where information about the slide cannot be extracted from the image, the image is presented to a user to that the slide information, such as its identity or the test to be applied, may be selected by the user to allow the slide to be processed.

12 Claims, 10 Drawing Sheets

U.S. PATENT DOCUMENTS

| | | | |
|---|---|---|---|
| 7,006,674 B1 * | 2/2006 | Zahniser et al. | 382/128 |
| 7,864,380 B2 * | 1/2011 | Descour et al. | 358/474 |
| 2003/0099580 A1 | 5/2003 | Pressman et al. | |
| 2003/0112330 A1 * | 6/2003 | Yuri et al. | 348/80 |
| 2004/0052408 A1 * | 3/2004 | Sharman et al. | 382/128 |
| 2004/0202577 A1 | 10/2004 | McNeil et al. | |
| 2005/0191214 A1 * | 9/2005 | Tseung et al. | 422/100 |
| 2006/0088928 A1 * | 4/2006 | Sweet et al. | 435/286.4 |
| 2006/0265133 A1 * | 11/2006 | Cocks et al. | 702/19 |
| 2008/0201082 A1 * | 8/2008 | Tohma et al. | 702/19 |

* cited by examiner

TISSUE SAMPLE IDENTIFICATION SYSTEM AND APPARATUS

FIELD OF THE INVENTION

The present invention relates to a method and system for sample identification and sample processing. In particular the present invention relates to tissue sample identification for tissue samples mounted on slides to be tested or processed in an automated tissue staining instrument.

BACKGROUND OF THE INVENTION

Histopathology involves the examination of tissue samples, for example human or animal, typically in the course of determining the disease state of the tissue or patient from which it was extracted. A typical process of preparing tissue for histopathological examination involves the following steps:

1. Removal of the Tissue from the Patient. This may be a surgical or other biopsy. This lump of tissue must be uniquely identified so that the doctor and subsequent handlers can identify the tissue and therefore patient that it came from, at a later date.
2. Processing the Tissue to fix it in Wax. This may be done in a tissue processor, and involves placing the biopsy in a container and placing the container in the processor, which replaces the moisture with wax, thus preserving the tissue. Also, the processed tissue is commonly placed on a support and embedded in a block of wax, to assist in the cutting of the tissue during the next stage. At this point the tissue is usually in a single piece and would have an identifier so that the patient and other data could be identified.
3. Creating the Slides. Typically the preserved and embedded tissue is placed onto a microtome and several slices of tissue are cut from the block, each useful slice being placed onto a slide. Usually information relating to the sample is reviewed to determine the number of tests to taken, which dictates the number of slides generated. At this point, the single identifier for the tissue is no longer useful as there are several samples on slides, each usually requiring the application of a different antibody or stain. Thus, each slide must be labelled so that the tissue sample from which they were cut can be identified, and also the individual test to be applied to the sample on the slide is associated with the label. This may be done by, for example, writing the slide information on a label applied to each slide.
4. Applying Antibodies to the Slide. On a Bond-maX instrument, information about each slide is entered into a computer controller, and a slide label is generated. The label may contain various types of information, but on the Bond-maX instrument, a unique identifier is printed onto a separate label, which is then placed onto each slide. The slides may have other labels from previous steps, but the label from the Bond-maX instrument must be the top label. Each slide is then placed onto the Bond-maX instrument, where the labels are scanned. When the labels are scanned, the instrument knows the test to be applied to each slide by the unique slide label identifier given to each slide. Other staining instruments may use a label containing information identifying the protocol (or test) to be applied. The instrument may automatically read the label to determine the test, or the user may place the slide onto an instrument, and instruct the instrument to perform the appropriate test to the slide.
5. Review of the Slides. A pathologist will need to review the slides to determine the disease state of the tissue. A single biopsy may have several sections removed for analysis, and therefore the pathologist may have to review a number of slides from a single patient. It is critical that the pathologist know which slides belong to the patient. In many cases the slides may be relabelled after testing on the various staining instruments to facilitate identification of the test applied, and also long term storage of the tested slides.

An individual laboratory, such as a pathology laboratory, may process a large number of slides, and the slides may come from a number of different providers, such as doctors or hospitals. Each provider may have their own method of labelling slides to identify the patient and test to be applied. The laboratory where the samples are sent for testing may therefore have to process slides having a number of different label formats. This prior art system allows different laboratories to provide slides with their own labelling system that may be run on a staining instrument, by relabelling for staining and relabelling again so that the label is identifiable by the doctors or hospitals system. This system is useful where a single staining instrument must test samples from a number of different sources, some or all of which are not compatible with the instruments information systems. However, information must be separately input into the instrument and labels must be printed and correctly applied to the slides before the slides can be tested.

Other systems, such as some Laboratory Information Systems, allow all the relevant information required to process a slide to be stored in a database, the pointer to specific information on the patient being contained on the slide label, for example using bar codes. However, this system requires that all the data from a variety of doctors be input into the laboratory information system, and requires all the instruments in the laboratory that require the information to be able to connect to the system to obtain the necessary data. It is useful to solve the problem of identifying slides uniquely where the slide identification system may not be compatible with the systems on the instrument.

SUMMARY OF THE INVENTION

The present invention seeks to provide improved method of identification of samples, improved methods of automating tissue processing, and apparatus therefore.

In one a method of sample identification is disclosed including the steps of:
  capturing an image of at least part of a sample support
  displaying said image on a screen for identification by a user.

The method may include the step of processing the image, where identification information
  in the image is either recognised and matches with processing information, or where the identification information is categorized as not identified.

The method may include the step of presenting an image of a sample that is not identified to a user.

By displaying the image on a screen, the identity of the sample can be confirmed. Further,
  once an image is categorized as not recognised, it can be highlighted to the user, and further identification can occur using the captured image.

The method may include the step of associating processing steps with the recognised image using information extracted from the image.

The method may include the step of presenting the user with a number of identifiers of samples.

The method may include the step of allowing the user to match the image of the sample not identified with an identifier, thus manually identifying the sample.

The method may include the step of presenting the user with identifiers of samples from the pool of identifiers that have been entered into a database, but not already identified.

The method may include the step of, where information within the image is automatically identified, associating the sample with processing information In another form a method of automatically identifying sample holders is disclosed, comprising the steps of:
 capturing an image of a label on a sample holder
 analysing the image to extract information about the image and where information is extracted, associating the information with the sample holder
 determining a protocol or test to be applied to the sample based on the information extracted from the image.

The method may comprise the step of
 analysing the image and extracting data,
 comparing the extracted data to identifiers in a database
 determining the protocol or test to be applied to the sample based on the contents of the database.

The method may include the steps of, where data cannot be extracted from the image:
 ascertaining the protocol or test to be applied to the sample by displaying the captured image to a user,
 allowing the user to select from a group of tasks not yet assigned to samples,
 wherein selecting a task determines the test or protocol to be applied to the sample.

In another form a method a method of identifying tissue samples on slides is disclosed comprising the steps of:
 capturing an image of containing information of a slide,
 assigning the image containing slide information a unique identifier,
 ascertaining whether the captured slide information is sufficient to initiate a process on the slide,
 requesting additional information required to complete the slide where necessary, assigning a protocol to the slide based on the information from the image and additional information.

The method may include the step of ascertaining whether the captured slide information is sufficient to initiate a process on the slide comprises analysing the image to extract slide information.

EXAMPLE OF PREFERRED EMBODIMENT

The embodiments shown in the figures relate to a sample, usually a thin section of human tissue, mounted to a microscope slide. In many pathology laboratories, microscope slides having tissue samples are tested by applying antibodies and/or stains to the tissue mounted thereon. The terms testing, applying antibodies, or processing maybe used interchangeably and refer to the process of applying a series of reagents to the slides to test if they have a particular feature. Pathologists then look at the samples on the slides, and from the placement and intensity of the staining, may make a determination as to the disease type and state of the tissue. Labelling of microscope slides for histopathology in particular presents unique problems, namely that there are many stages of processing required from the extraction of the tissue sample from the patient to the eventual staining of the antibodies by an instrument, such as the Bond-maX instrument. In the process of removing a patient sample to the eventual viewing of the slide by a pathologist. the sample itself may be labelled a number of times, be placed in several different devices for processing, and then have sub-samples removed from the main sample. Each sub-sample may have a different test applied, and each must be correctly associated with the original sample and patient. This has resulted in a number of labels being applied to a single slide. Examples will be discussed which reduce the need for multiple labelling.

Figure 1:
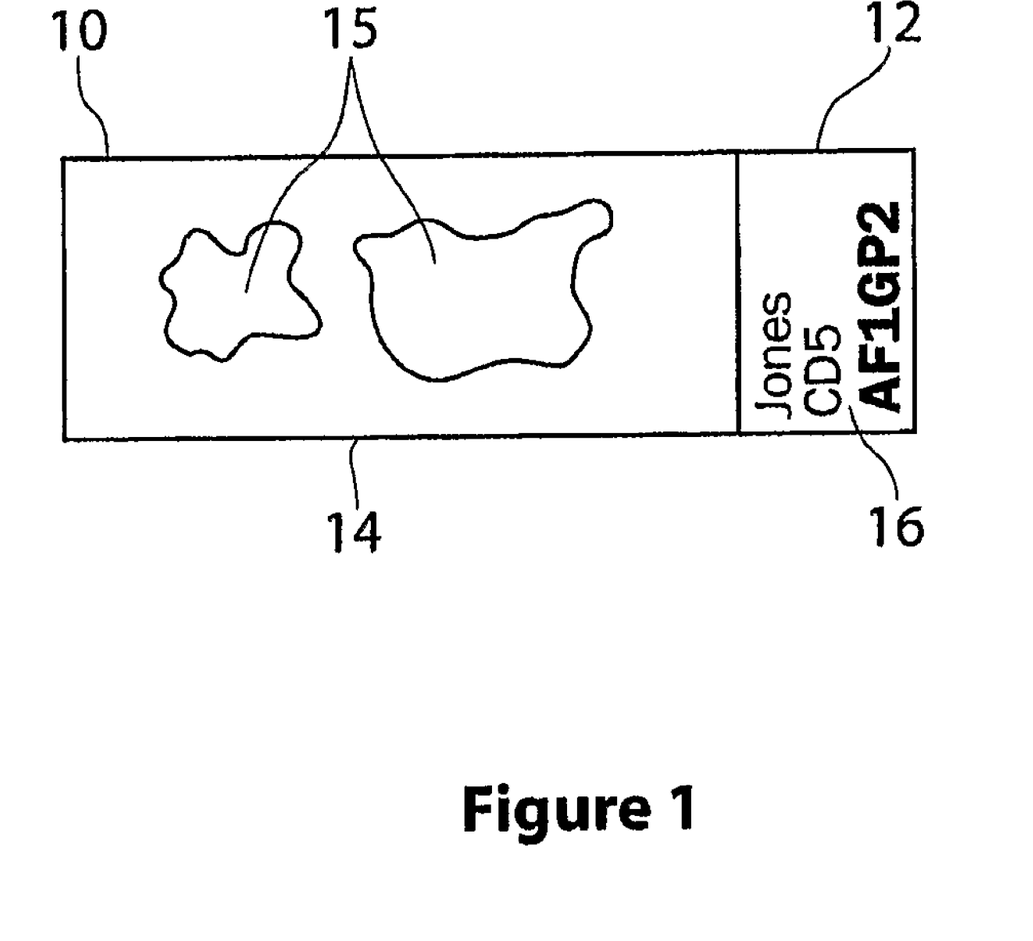
FIG. 1 shows a slide having a tissue sample and a label
Figure 3:
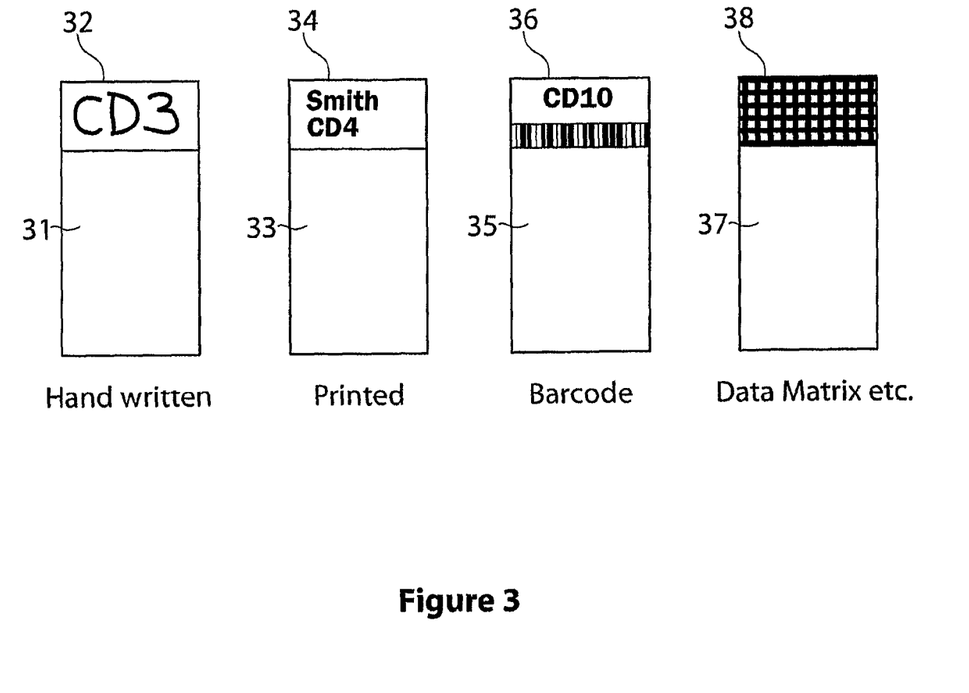
FIG. 3 shows examples of slide label formats.

FIG. 1 shows a slide 10 having an identification region 12 and a sample region 14. A sample 15 is mounted to the slide 10 in the sample region 14 in a known manner. The identification region 12 may contain information sufficient to identify the slide to various systems or users. In FIG. 1, a slide identification region 12 contains a label 16 which includes a number of fields, in this case a name (e.g. patient), a primary antibody to be applied during the test (e.g. CD5 as sold by Novocastra Laboratories Ltd) and a unique identifier in the form of a character string. The unique identifier may be machine readable characters, a bar code, an infoglyph, or other form of unique identifier capable of being visually identifiable to a person and/or instrument. Additional examples are shown in FIG. 3.

The label 16 may be printed onto adhesive paper and applied to the slide, or may be etched or printed directly onto the slide. Other known methods of identifier may also be used, including but not limited to non visual means such as RFID chips and magnetically encoded strips. If the identifier is non-visual, then some method of visually labelling the slide may be included.

Labels may contain only a unique identifier, protocol or test information, other information as required, or a combination of information and identifiers.

Figure 2:
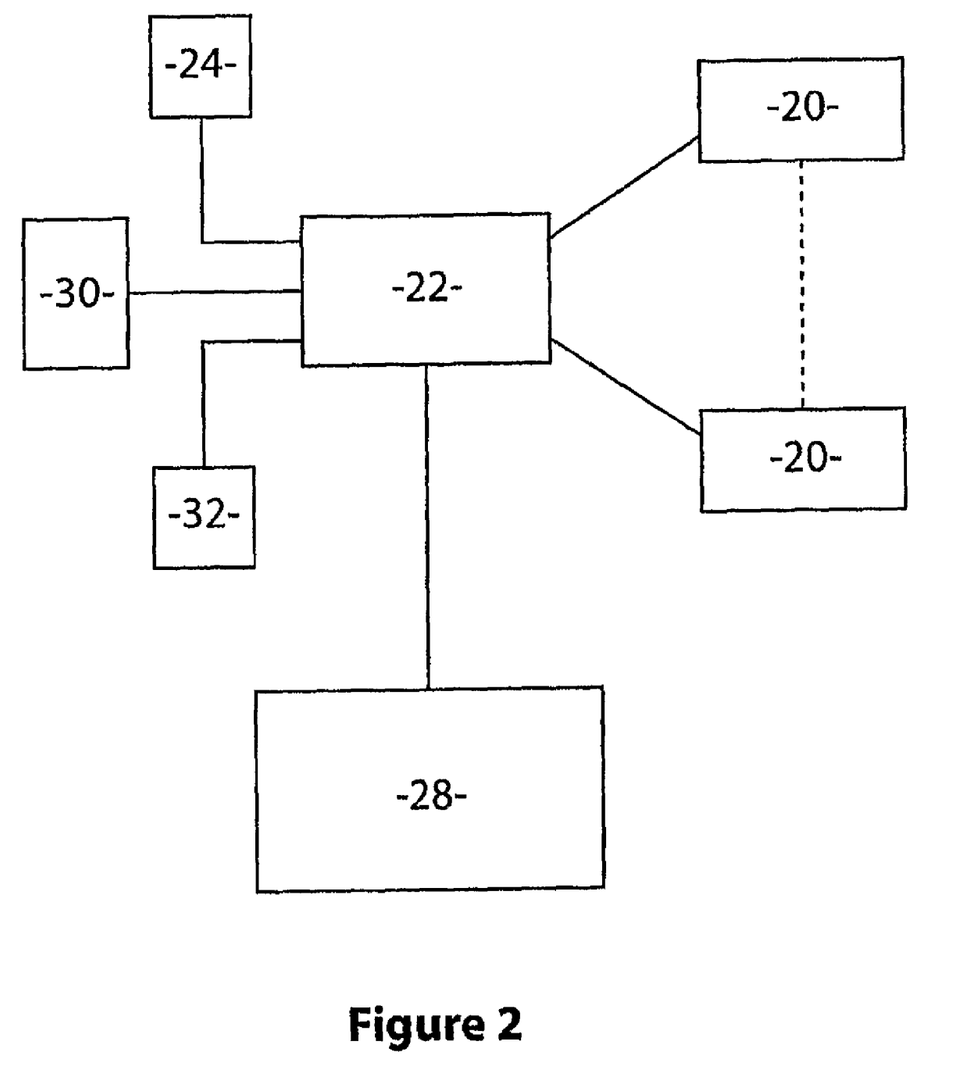
FIG. 2 shows a schematic layout of the system of the present invention.

In FIG. 2, a schematic set up of a staining instrument such as a Bond-maX instrument is shown. One or more processing modules 20 (for example a Bond-maX processing module) are connected to a controlling PC 22. The controlling PC 22 runs software to control the modules 20, and may have a database for storing information about the slides to be processed. The controlling PC may be a standard personal computer as sold by Dell. Laboratory Information System (LIS) 28 may also be connected to the controlling PC 22. Data from the LIS may be used to populate the database with data, and the laboratory information System 28 may also request status information from the controlling PC 22 in a known manner. Also connected to the controlling PC may be a scanner 24 and a printer 30. The scanner 24 may be a bar code scanner for reading reagent containers that are used in the testing of the slides (as described in PCT/AU2003/00779) or may be an imager able to capture images of reagent containers for similar purposes. The printer 30 is preferably adapted to print slide labels as described below. Input device 32 may be in the form of a keyboard, to input data into the controlling PC 22.

Figure 9:
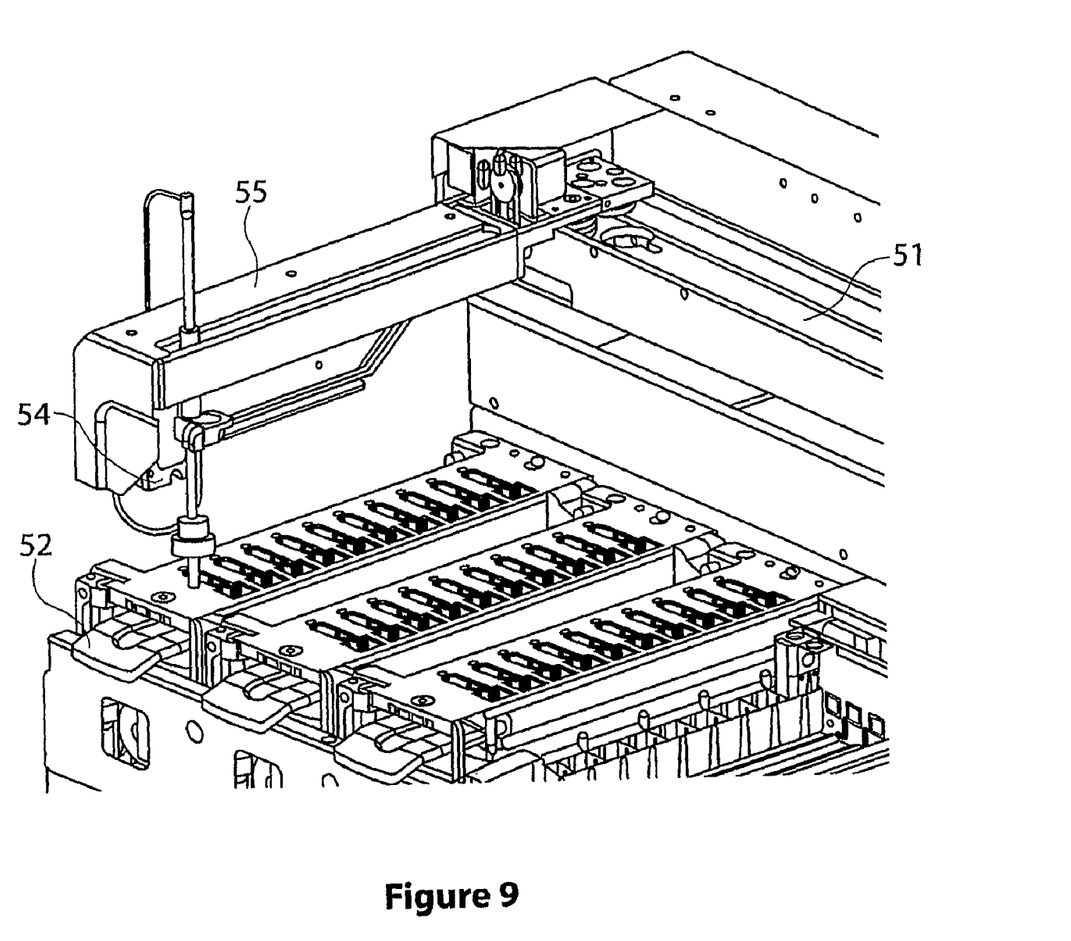
FIG. 9 shows a portion of an automated tissue staining system.

Tissue samples 15 on slide 10 may be processed on an instrument such as a tissue stainer as described in PCT/AU2003/00779 or sold under the name Bond-maX by the applicant. Before the tissue can be processed, the instrument needs to ascertain what test is to be applied to the slide in question. On the abovementioned instrument, up to 30 slides may be loaded on three batches of ten slides at once for simultaneous processing, or processed in individual batches of up to 10 slides. In the present example, slides are loaded into a slide tray 50 which may hold up to 10 slides. FIG. 9 shows a partial cutaway of a Bond-maX instrument 51. In FIG. 9 tray 50 is loaded into the instrument 51 for processing.

Before processing, information relating to the slides must be identified. Information about the tests to be applied will be determined before slides are to be tested. Tests may include routine staining such as Haematoxylin and Eosin, and may also include for example immunohistochemistry tests, in-situ hybridisation tests, or other tests applied to slides. Each slide must be associated with sufficient information to ensure that the correct test is applied. Examples of methods used to collate data are described below.

There are a number of ways of automatically processing slides. One way is to have all the data already input into either the instrument that performs the test (for example instrument 51) or a database connected to the instrument to perform the tests. In this way when a slide is loaded onto the instrument, the instrument may collect information about the slide and perform the appropriate test.

In another embodiment, the data is not entered into a database before the slide is loaded. In such a case, for automated operation of an instrument to test the slide, the information may need to be either directly entered into the instrument (or associated database) after the slide has been loaded. Alternatively the slide may have a label that tells the instrument the protocol to apply, for example the various protocols that may be applied are embedded in the instrument or associated system, and upon reading the label, the correct protocol can be applied.

The labels may be pre-printed with information as described previously, or may be labels from other systems but necessarily containing unique identification recognisable by the instrument, or may be labels from other instruments not containing unique identification, or alternatively, maybe handwritten labels containing no unique identification recognisable by the system.

Figure 8:
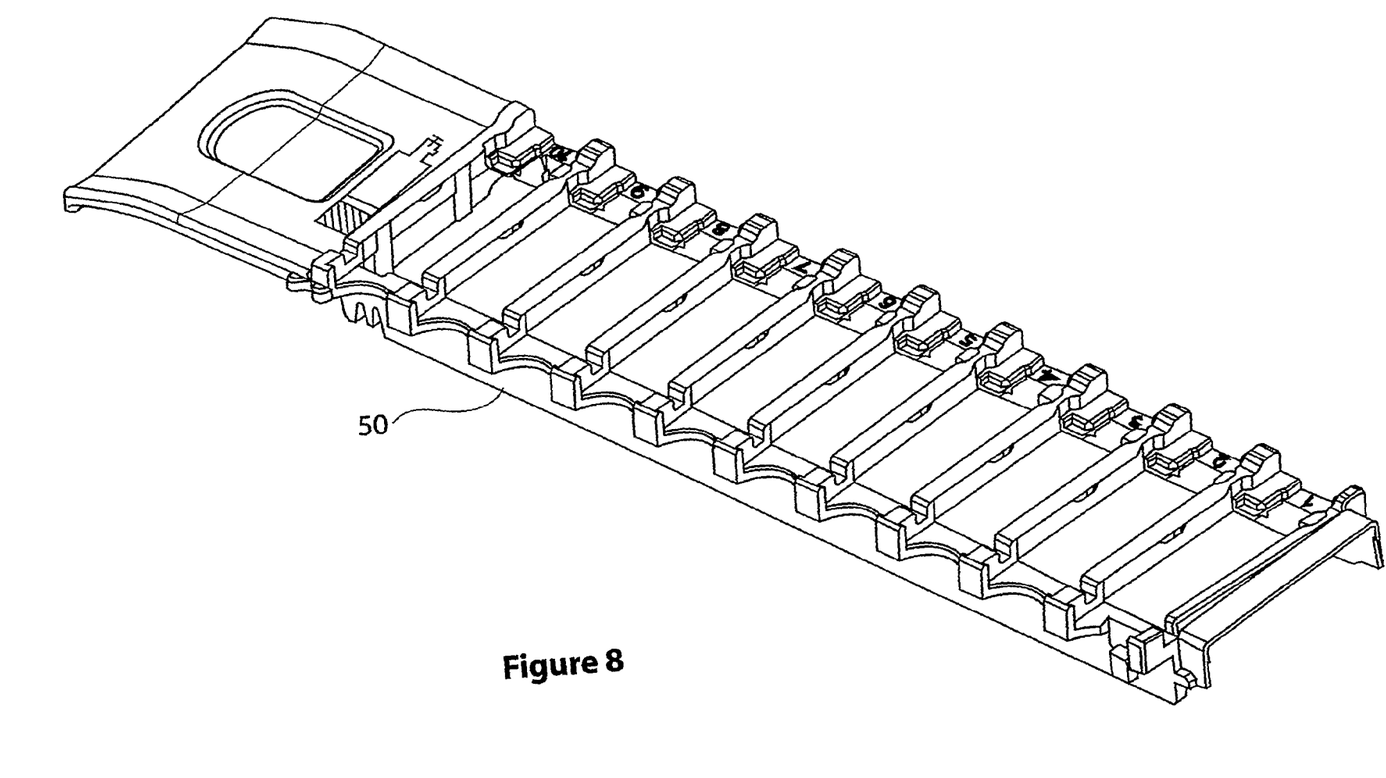
FIG. 8 shows a slide tray for use on an automated tissue staining instrument

In one embodiment shown in FIG. 1, each slide 10 has a label 16. In FIG. 3, example slides 31, 33, 35 and 37 are shown. If slides 31, 33, 35, and 37 are loaded onto a tray 50 (shown in FIG. 8) and the tray 50 is loaded onto the instrument 51 as shown in FIG. 9, then an image capture device 54 such as a digital camera or imager moves from slide position to slide position capturing an image of each label.

Figure 4:
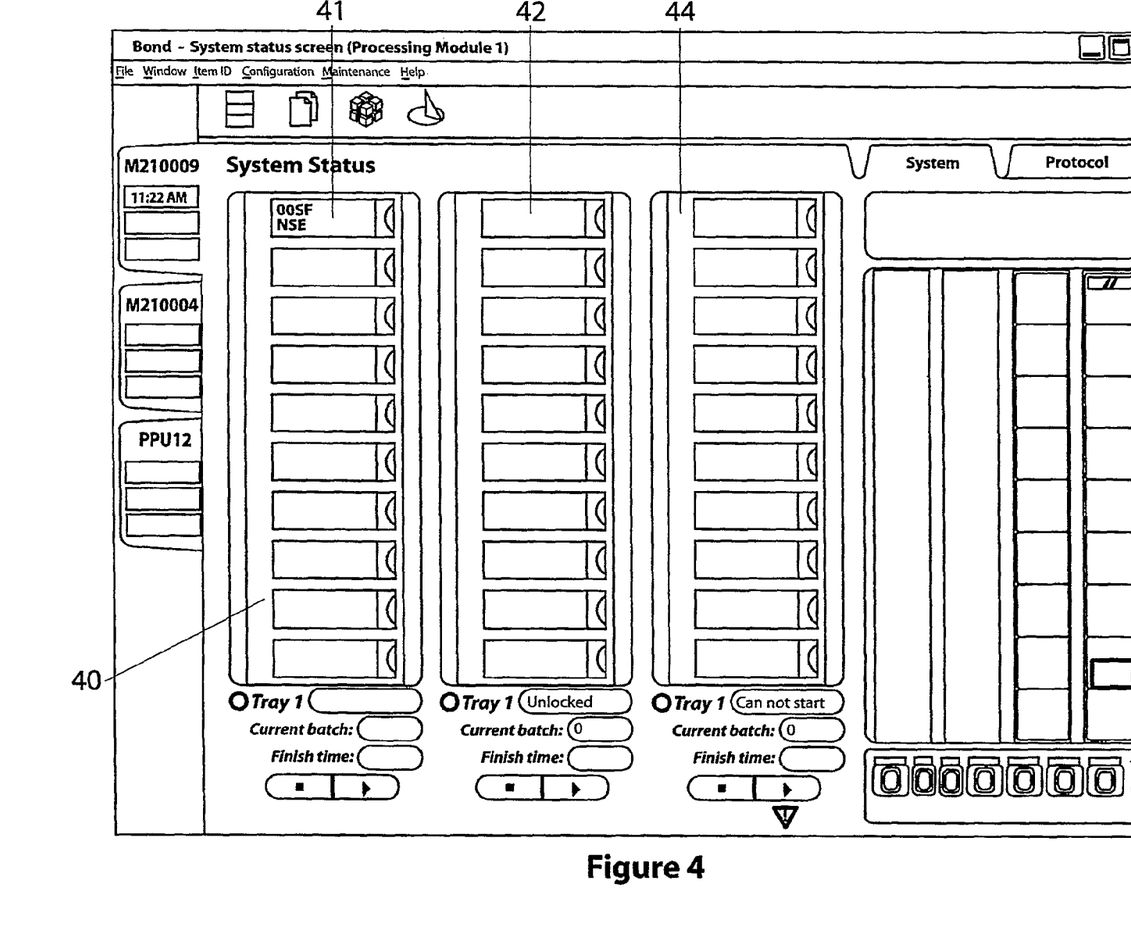
FIG. 4 shows a first image of a computer program window of a software program of the system of the present invention.
Figure 5:
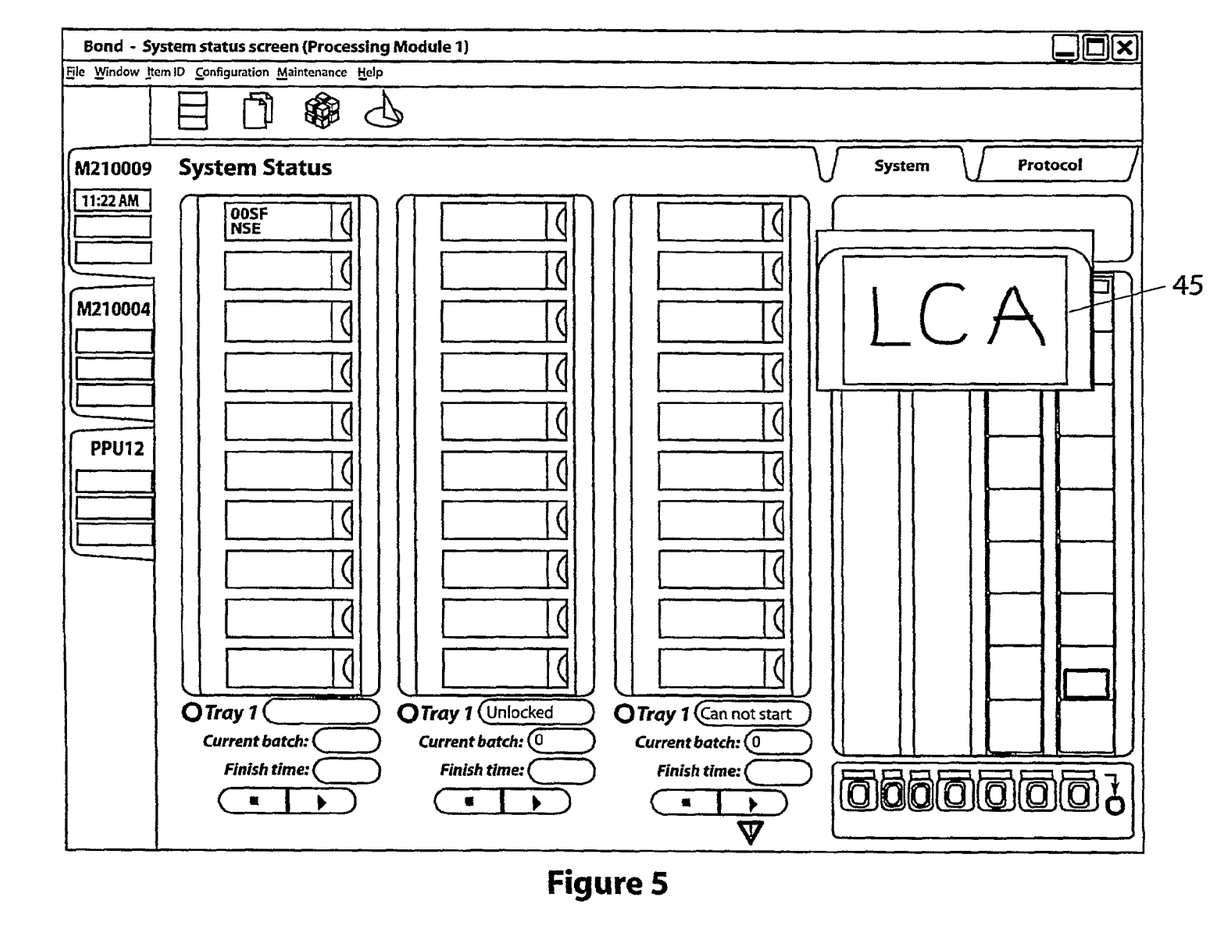
FIG. 5 shows a second image of the computer program window of the software program of the system of the present invention.

In one of the methods described above, data has already been entered into a database, which in various known methods, is connected to the Bond-maX instrument or its controller. When an image is taken of each slide, the image is processed (either on board the Bond-maX instrument, or externally) and if data can be extracted from the image, it is compared with known data in the database. For example, the labels may have unique identifiers in the form of machine readable text. An optical character recognition program may be run on the image of each slide to extract information relating to the machine readable text, in order to uniquely identify the label and therefore the slide. The extracted information from each image is compared to a list of identifiers for known slides. Matches are made wherever possible, and in many cases (where slides labels have been generated by a printer 30 associated the instrument 51) usually all the slides will be correctly identified. In such a case a GUI as shown in FIG. 4 of the present example may display a representation of the recognised slide labels showing information such as the slide identifier, test information etc, as shown in FIG. 5.

In some cases, the labels may not be machine readable even though they were generated to be read by the instrument. This typically occurs where fluid has been spilled on a label, or it has been applied incorrectly to the slide. In other cases the labels may be generated by other instruments, or the information may be handwritten. In such a situation, if the image of the label does not contain information that can be extracted by the instrument 51, or information that when extracted, does not correlate to a known slide, the slide cannot be processed, as the instrument does not know which test to apply. In such a case the following method may be employed.

After failure to extract appropriate information from an image of a slide, the slide is highlighted by the GUI as not being correctly identified. A user can select the slide, for example by clicking an image of the slide with a mouse pointer, and may be shown an image 45 captured of the slide label, as shown in FIG. 5. In some cases the user will be able to identify the slide by looking at the image, given that the human eye is generally more capable at recognising certain information within images than some commonly available optical character recognition programs. In the example of FIG. 5, the label is handwritten with the characters "LCA". If the user can recognise the slide or test to be applied, then data identifying the slide (or perhaps just the test to be applied) may be entered into the computer so that the instrument knows what test to apply. In the case of the Bond-max instrument, records of the slides processed are recorded using a unique identifier for each slide to associate the test with the slide. In such a case a unique slide identifier may need to be entered, and the instrument may prompt the user to enter a unique identifier, or allocate one to it. Also stored with the unique identifier may be test data including reagent information such as expiry date and batch, and also a copy of the image so that verification can be undertaken at a later date.

In another embodiment, once an image has been captured but where it cannot be identified, the user may select the image, then call up a list of all the slides that have had data entered (or slides printed) but have not yet been identified as loaded onto the instrument. The image could then be associated with one of the slide identifiers. This could be accomplished by dragging a protocol or slide identifier onto the image so that the instrument knows what protocol to apply to the slide, and that information may also be associated with a unique identifier that records the protocol applied to the slide. The database containing the list of slides may be resident on the Bond-maX system, or external to it, accessed over a network or other known method.

The method of identifying slides using an image has numerous benefits. One benefit is that there may be hundreds of slides processed per day, and if only a few images are not recognised, it may take a substantial period of time to look through all the records to ascertain which is the slide that is not recognised.

FIG. 3 is an example of slide identification from a captured image of a slide label. In slide 35, a bar code is located on the slide label 36. An image of the bar code is taken and may be subjected to image analysis to extract information from the bar code, such as a slide or tissue identification umber, protocol or antibody to be applied, other information or a combination of information. The information from the bar code may be extracted, and if the format of the bar code is known (that is, what fields are contained with in the bar code) then those fields containing relevant bar code information can be automatically extracted to fill the fields of the unique slide identifier in a case. Alternatively, the bar code may only be a unique identifier which allows the computer to access the required slide data information from the slide data database by matching the unique slide identifier to one of the field in the database.

In slide 37, a data matrix is provided on slide label 38. If the format of the matrix is known then the image captured can be analysed and the relevant information extracted and associated with slide data in a similar way to that described for slide 35.

In each of the above cases, where information is automatically extracted from the image, the operator may be prompted to check the data for accuracy and confirm that the data in each field is correct before proceeding or closing the case. Having the image of the slide label next to the slide data enables a direct comparison to be made.

When all the relevant slides have been loaded and information in relation to those slides has been entered into the files in the database and the cases closed, the instrument can commence processing the slides in accordance with the information in the database. Once processed, the test information in relation to each slide can be written to the fields in the database associated with the relevant unique slide identifiers. In this way each slide, regardless of label system employed, will be processed and have a database of information in relation to the test applied, including information such as an image of the slide, the type of reagent applied, batch number and expiry date of reagent, specific protocol employed, instrument number, date and time of test, and other information. This information may be sent back to the provider with the slide so that the provider can check that the correct test was applied. The image of the slide label may also be printed to assist identification of the slide.

FIG. 4 shows a screen capture of the Bond software used to control the Bond instrument. The window includes displays of the three trays that may be loaded onto an instrument. Tray window 40 has one slide registered, shown as slide image 41. The slide in this tray has been recognised by the instrument and is ready for processing. Tray window 42 indicates that no tray has been loaded, and all slots are without images as no images have been captured. Tray window 44 shows images captured from a slide tray 50 loaded into the instrument 51 as shown in FIG. 9. In use, a tray is loaded into a instrument and the instrument captures an image of each slide position to ascertain whether there is a slide to be processed. In slide tray window 44 there are four images of slide labels captured, and six empty tray positions. The empty positions also have an image captured however the image contains no slide data only an image of the support that locates the slide. This enables the user to confirm that the slide position in the instrument is in fact empty, as opposed to containing a slide that has not been recognised. As the processing module and controlling computer may be separated by some distance, and also there may be 5 or more processing modules connected to one controlling pc, it is not always a simple matter to review each slide on an instrument.

Figure 6:
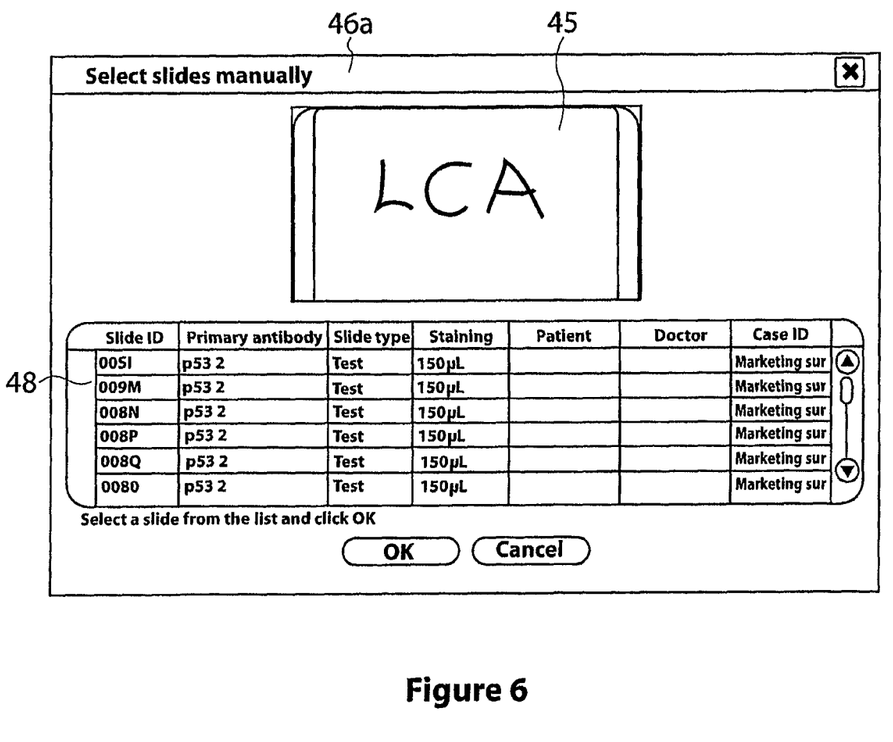
FIGS. 6 and 7 and 7a show further images of the computer program window of the software program of the system of the present invention.

In FIG. 5, the second slide image 45 is magnified so the operator can view information on the slide label of the particular slide loaded into the instrument. In this instance the slide label has had LCA hand written onto the slide label. This may identify the slide or the particular protocol or reagent to be applied to the tissue sample on the slide. In FIG. 6, the operator has selected the slide label 45 displaying LCA and a new window 46 has been generated on the screen of the monitor. The slide image 45 represents the slide loaded into the instrument. In the present case the slide is loaded into the instrument in tray position 3, and the slide is the second slide position in the tray 50. The image capture device in the Bond instrument is mounted on a robot arm which moves from slide position to slide position to capture all the images of the slides after a tray has been loaded. In this way the instrument knows the location of each slide loaded onto the instrument because it knows and controls the location of the image capture device 54 mounted onto the robot arm 55 shown in FIG. 9. In other embodiments, the image capture device may capture a number of slide labels in one image and ascertain the location of the slides by the location of the slide labels in the image.

Window 46a displays a pane 48 having a list of slide data that was already entered into the computer database. The operator selects the slide data containing the correct test for that slide, and the slide in the instrument is allocated the particular slide ID, and the protocol in the slide data is associated with the slide on the instrument 51. The instrument 51 then knows which protocol (reagents and antibodies) to apply to the particular slide. If there is no data associated with the slide in the instrument, the operator may choose a new data field and enter the data manually to allow the slide to be processed. A slide cannot be processed until sufficient data has been entered onto the system.

Typically a provider such as a hospital will send a number of slides and associated test request information relating to each of the slides, to a laboratory. The laboratory will then enter the test data into the database where it can be associated with a slide as shown in FIG. 6. The data may be entered manually from a list sent to the laboratory, or the data may be loaded from a storage medium such as a CD, or the controlling computer may be connected to a database of the provider to access the test data directly.

Figure 7:
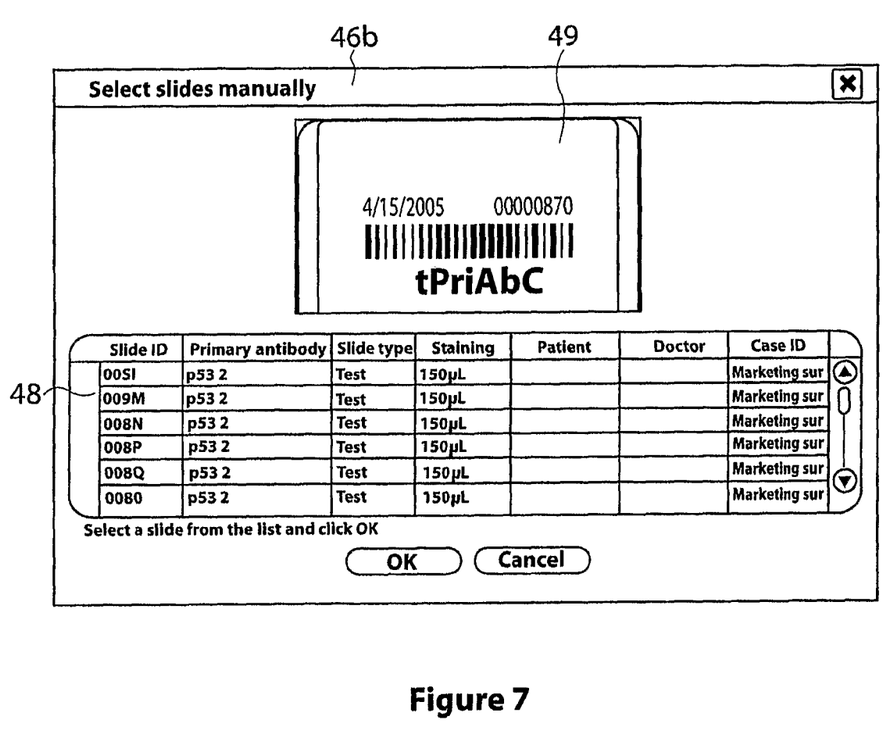

In another embodiment shown in FIG. 7, another slide having significant information has been selected and the slide image 49 is shown in window 46b. Slide image 49 contains a date the label was printed, a unique slide identifier (00000870) a bar code and an antibody indicator (tPriAbC). This data can be used to identify the slide to the operator to allow selection of the required test information from the list of slide data shown in pane 48. In another embodiment, image processing may be employed on the image 49 to enable information from the bar code (or other text data) to be automatically extracted and correlated to slide data. Image processing may also be used to automatically select or verify the antibody to be applied to the slide. When the image is associated with the slide data, a copy of the image is attached to the selected filed in the database for verification purposes. Also stored in the database is information relating to the test performed, such as type of reagents used, reagent batch numbers, expiry dates, identification of the instrument, such as type and serial number, date of test and other useful information. This information can be used for verification purposes at a later date as required, and may be sent back to the provider with the processed samples.

Figure 7A:
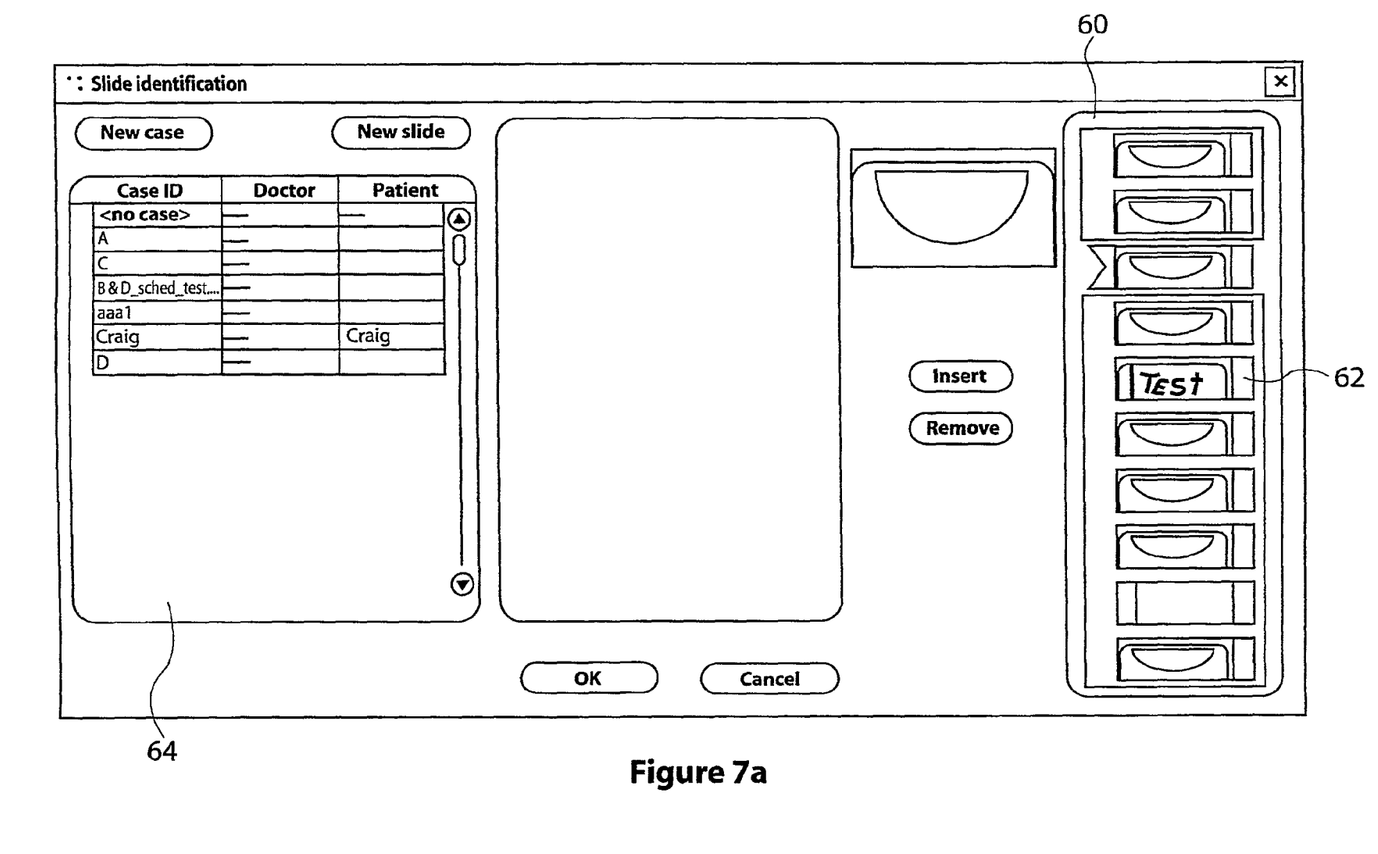

In another embodiment shown in FIG. 7a, a tray of slides has been scanned but in this case no slides have been recognised, as shown by the representations of the slides loaded in region 60. The first four positions show images of the slide supports, indicating that there is no slide in each of those positions. Slide position 62 in the figure shows that an image of the slide label has been captured and put onto the screen. In this embodiment, there is no unique representation for the slide that is recognisable by the particular embodiment of software of the controlling PC. The user may now enter in details of the tests to be performed by adding a new case to the database. A case usually relates to an individual patient requiring a group of tests, or some other group of tests to be performed. A number of slides may be from a single patient and these are usually all added in under a single case. In the example shown in FIG. 7*a*, a window 64 in the GUI shows a number of previously allocated cases. If one of these is appropriate, then it may be selected. Predefined cases may have one or more slide processes identified. If there is only one slide process allocated to a case then that process will be matched to the selected slide. If there is more than one process the user can select the slide process to be applied to the slide. Once selected and associated with a slide loaded onto the instrument, that slide process within that case will no longer be available for selection. Alternatively if no case is appropriate then the user may define a new case by selecting the slide image shown in region 60, pressing the new case button on the GUI, then when the case has been created, adding a slide so that details of the test to be applied to the slide are identified, which will allow the slide to be processed. Typically a copy of the image will be stored with the case details. During or after processing, details of the processing may also be stored with the slide data.

In another embodiment, not shown, the slide label may have a case identifier rather than a unique identifier. This case identifier will not identify the specific process to be applied to the slide, but will identify the slide as belonging to a group, typically from a single patient. When the slide is loaded into the instrument and the image is captured, the case details will be shown, including a number of tests that may be required to be applied to various slides. The user may select a particular test, which is associated with the slide, and this test will be applied to the slide. In one embodiment that specific test will then be removed from the list of allowed tests to be performed on other slides having that particular case identifier. For example, if a case for a patient requires 5 different tests, then 5 would be generated, and labels applied to each. The slides may have the same case identifier encoded into the label information, in the form of a bar code or optical characters. Other details may be included, for example an element to identify the slide within the group of slides from the same case. Once each slide is loaded and an image captured, one may be selected whereupon, provided the system has been able to extract the case identifier from the image, the case will be shown in window 64. One or more slide tests will then generally be available for selection and once selected the instrument can process the slide.

The above methodologies allows the instrument to use slide labels from a number of different providers, all of whom may chose to use different slide identifiers. It does not necessarily require the slides to be relabelled to operate on the instrument, and thus may make processing slides on the instrument faster (no relabelling) more accurate (no chance or relabelling the wrong slide) and/or more flexible (can use anyone's slide identification system). Further, verification is provided as the image of the slide label is associated with the test data and therefore it is possible to verify that the test indicated on the label (either directly or via a slide identifier) was the test applied.

In the Bond-maX system, the imager used to capture the image of the slide label is a HHP imageteam 4600-ocr/bar code scanner. The software that may be used is Smart Reco-S by Recoscript GMBH. The analysis may be conducted in firmware or software, and may be undertaken onboard a capture card mounted to the imager, or the imager may take the image, and send it to a computer, such as for example, a computer on board the processing module of the Bond=-maX instrument, or a controlling PC of the Bond-maX instrument. In the currently preferred embodiment, the image is captured by the Jadak imager, and sent to the controlling PC where software is used to extract information from the image. In the preferred embodiment, a label may contain a number of information fields, yet the imager may require only one field to determine the identity of the slide. In such a case, the imager may only analyse a certain proportion of the image to extract the required details. In FIG. 7 a label is shown having a number of fields including a bar code. The software may analyse the image and only select a window around the bar code, so that other information, not required for slide identification (such as the antibody type, date, etc) does not affect the reading of the bar code. A similar window can be applied if optically recognisable characters are used instead of bar codes. Optically recognisable characters are useful as they can be read by the user, whereas bar codes can only be read by machines. Thus, if human and machine-readable OCR characters are used, and the imager fails to extract the unique identifier from the label, the user can attempt to read the label and identify the slide manually by looking at the GUI displaying the images. In this way, the user does not need to attempt to read slides that are loaded onto the instrument, and then try to remember their exact location so their identifier can be entered manually into the instrument. The above example is typically used where slides are printed in a predetermined format so that the instrument knows approximately where to look for the slide identifier. If the slides were handwritten, the imager may choose to analyse the whole image to extract identification data.

In one form (not shown) the slide label may have a some identifying information, but the slide may also contain a non visual method of identification, for example magnetic stripe or rfid chip. If an instrument has a reader adapted to read the non-visual identification means, and it fails to read a identify the slide in a particular position, then the image captured of the slide label may be used to identify the slide by the methods and apparatus described herein.

From the above it is apparent that there are advantages to a method and system for sample identification. Presenting a slide with optical characters that are human readable and machine-readable increases the space available for information, as the slide label does not need to have a bar code. Even if the label has a bar code, but preferably human readable characters, presenting an image on the screen of a controlling PC allows data to be matched with that sample in a way where the positional information of the sample is known by the instrument, and if information is not able to be extracted from the image, then data relating to unmatched samples can be viewed to determine whether there is a match. This simplifies the matching process and reduces errors. As the image may be stored with the sample data, later confirmation that the data matched to the sample is possible.

Other advantages include that the imager captures an image of where the slide would be placed after a tray is loaded onto the instrument. In a preferred embodiment, there is a slide tray for holding slides, and a sensor in the instrument that detects when the tray has been loaded. After loading the robot arm holding the imager moves to each position and takes an image of each slide position. Where there is no slide, the software may recognise that there is no slide and allocate that slide position to empty. Alternatively there may be an image displayed so the user can determine whether there is a slide in the tray position or not. This is useful as if the image is not presented, merely an error or no information about that slide position, the user has to physically look at the slide in the tray loaded onto the instrument. On many instruments, there may be physical obstructions to easily viewing the slide position, and it may also be difficult to read specific slide identifying information if the label was not automatically identified. Of course the present invention works equally as well if there is no slide tray and slides are loaded directly onto slide supports. The present system is able to be implemented on other automated tissue staining systems that employ an image capture device, and is not limited to instruments sold by the applicant.

The claims defining the invention are as follows:

1. A method of sample identification, the method comprising:
    capturing an image of at least part of a sample support;
    processing the image to determine whether identification information in the image is identified as matching with processing information;
    when the identification information is not identified, displaying said image on a screen for identification by a user; and
    presenting the user with a list of identifiers representing identification information of sample supports when the identification information is not identified.

2. The method of claim 1, further comprising associating processing steps with the image using information extracted from the image.

3. The method of claim 1 further comprising allowing the user to match the image of the sample support not identified with one of the identifiers to manually identify the sample.

4. The method of claim 1 wherein the list of identifiers includes those identifiers from a pool of identifiers that have been entered into a database, but which have not already been associated with a sample support.

5. The method of claim 1 further comprising when identification information within the image is automatically identified, associating the sample with processing information.

6. A method of automatically identifying sample holders, the method comprising:
    capturing an image of a label on a sample holder and analyzing the image to extract information from the image;
    when information is extracted, associating the information with the sample holder and determining a protocol or test to be applied to a sample on the sample holder based on the information extracted from the image;
    analysing the image and extracting information;
    comparing the extracted information to identifiers in a database;
    determining the protocol or test to be applied to the sample based on the identifiers of the database; and
    when information cannot be extracted from the image:
        ascertaining the protocol or test to be applied to the sample on the sample holder by displaying the captured image to a user, allowing the user to select from a group of tasks not yet assigned to any other sample holders, wherein selecting a task determines the test or protocol to be applied to the sample holder.

7. A method of identifying tissue samples on slides, the method comprising:
    capturing an image containing information from a slide,
    assigning the image containing the slide information a unique identifier,
    ascertaining whether the captured slide information is sufficient to initiate a process on the slide,
    requesting additional information required to complete the slide when the captures slide information is insufficient, and
    assigning a test protocol to the slide based on the information from the image and additional information.

8. The method of claim 7 further comprising ascertaining whether the captured slide information is sufficient to initiate a process on the slide comprises analysing the image to extract the slide information.

9. An apparatus for processing samples comprising:
    an imager that captures an image of at least a portion of a sample support containing a sample;
    a display that displays the image;
    a processor that processes the image to determine whether identification information in the image is recognized and matches with processing information,
    when the identification information is not identified, displaying the image on the display for identification by a user,
    wherein in response to the image being determined to be not identified, information is displayed to the user that comprises a list of identifiers representing identification information of sample supports.

10. The apparatus of claim 9, wherein in response to the processor determining that the image is recognized, the processor associates processing steps to be performed on the sample.

11. The method of claim 9, wherein the list of identifiers includes those identifiers from a pool of identifiers that have been entered into a database, but which have not already been associated with a sample support.

12. A method for processing a sample on a slide using an automated tissue staining instrument having an imager for capturing identification information from a slide and a testing portion for testing the slide based on identification information, the method comprising:
    loading a slide with a tissue sample disposed thereon into the automated tissue staining instrument, where identification information is on at least a portion of the slide;
    capturing an image of the identification information to determine whether the identification information is identified as matching with processing information;
    displaying the image on a display if the identification information is not identified and obtaining the identification information related thereto;
    testing the sample on the slide based on the identification information, wherein the testing comprises at least applying a reagent to the slide.

* * * * *